United States Patent [19]

Tohmatsu et al.

[11] Patent Number: 4,757,000

[45] Date of Patent: Jul. 12, 1988

[54] PROCESS FOR ASSAYING ATL VIRUS ANTIBODY AND REAGENT THEREFOR

[75] Inventors: Junichi Tohmatsu, Tsuchiura; Takashi Sawada, Yatabemachi; Isao Miyoshi; Hirokuni Taguchi, both of Kouchi, all of Japan

[73] Assignee: Eisai Co., Ltd., Tokyo, Japan

[21] Appl. No.: 736,928

[22] Filed: May 22, 1985

[30] Foreign Application Priority Data

May 25, 1984 [JP] Japan .................... 59-104472

[51] Int. Cl.⁴ ............... G01N 33/543; G01N 33/574
[52] U.S. Cl. ............................... 435/5; 435/4;
  435/7; 435/820; 435/948; 436/520; 436/522;
  436/531; 436/542; 436/813; 935/110
[58] Field of Search ........... 435/4, 5, 7, 820, 948;
  436/520, 522, 531, 542, 813; 935/110

[56] References Cited

U.S. PATENT DOCUMENTS 4,588,681 5/1986 Sawada et al. .................. 435/5

FOREIGN PATENT DOCUMENTS 2122343 1/1984 United Kingdom ............... 435/7

OTHER PUBLICATIONS

Yolken, "Reviews of Infectious Diseases", 4(1), pp. 35 and 45–48.
Kobayashi et al, "Genomic Structure of HTLV", Chem. Abstr., vol. 101, 1984, #66926s.
Okai et al, "T Cell Growth Factors", Chem. Abstr., vol. 102, 1985, #43754r.
Miyashi et al, "Type C Virus in a Cord T-Cell line", Nature, vol. 294, Dec. 1981, pp. 770–771.
Okai et al, "T-Cell Growth Factors", FEBS Letters, vol. 177, No. 2, Nov. 1984, pp. 200–204.
Miyoshi, I., et al, Gann, 71, 155 (1980).
Miyoshi, I., et al, Jap. J. Clin. Oncol., 9 (Suppl.), 485 (1979).
Miyoshi, I., et al, Gann, 73, 399 (1982).
Miyoshi, I., et al, Lancet, 683 (1982).
Shimoyama, M., et al, Jap. J. Clin. Oncol., 12 109 (1982).
Miyoshi, I., et al, Gann, 72, 978 (1981).

Primary Examiner—Esther M. Kepplinger
Assistant Examiner—Robert Benson
Attorney, Agent, or Firm—Flynn, Thiel, Boutell & Tanis

[57] ABSTRACT

An improved assay for an ATL virus antibody in a specimen, in which an ATL virus antigen is added to the test specimen and used as a comparative specimen. This improved method selectively assays ATL virus antibodies, and, thus, is useful in preventing and treating adult T cell leukemia.

4 Claims, No Drawings

PROCESS FOR ASSAYING ATL VIRUS ANTIBODY AND REAGENT THEREFOR

This invention relates to a process for assaying ATL virus antibodies and a reagent therefor. By the term "ATL virus" is meant adult T cell leukemia virus, which is also abbreviated as "ATLV". ATL virus and ATL virus antibodies to be assayed in the present invention are described in detail in the following literature are incorporated herein by reference thereto:

(1) Miyoshi, I., et al., Gann, 71, 155 (1980).
(2) Miyoshi, I., et al., Jap. J. Clin. Oncol., 9 (Suppl.), 485 (1979).
(3) Hinuma, Y., et al., Proc. Nat. Acad. Sci., 78, 6476 (1981).
(4) Miyoshi, I., et al., Gann, 73, 399 (1982).
(5) Miyoshi, I., et al., Lancet, 683 (1982).
(6) Shimoyama, M., et al., Jap. J. Clin. Oncol., 12, 109 (1982).
(7) Ohkouchi et al., Immunohaematology, 3 (5), 267 (1983).

The need for assaying ATL virus antibodies, a process for preparing an ATL associated antigen required for the assay, a process for assaying the ATL-virus antibodies with the use of said antigen and a reagent therefor are disclosed in detail by Japanese Patent Laid-Open No. 62527/1984 corresponding to U.S. Ser. No. 535,457, filed Sept. 23, 1983, now U.S. Pat. No. 4,588,681, which is also employed as a literature reference herein.

The above literature references indicate that a significantly large number of blood transfusion donors carry the ATL virus so that there is a possibility that blood transfusions may play an important role in the transmission of said virus. Thus, it is necessary to assay ATL virus antibodies in the serum of donors to screen ATL virus carriers, thus preventing infection by blood transfusion, and to provide a highly sensitive process for assaying said antibodies and a reagent therefor.

Under these circumstances, Japanese Patent Laid-Open No. 187861/1983 corresponding to U.K. Patent application No. 2122343A, has disclosed a process for assaying ATL virus antibodies by enzyme immunoassay or radioimmunoassay with the use of ATL associated antigen producing cells. Japanese Patent Laid-Open No. 62527/1984 as cited above has further disclosed a process for assaying ATL virus antibodies wherein an ATL associated antigen is prepared by treating ATL associated antigen producing cells with a surfactant and a reagent therefor.

These ATL associated antigen producing cells and the ATL associated antigen are prepared by partially purifying them and contain various non-specific antigens besides the ATL virus antigen. Thus, an assay wherein either of these materials is employed might result in the detection of not only the ATL virus antibodies but other non-specific antibodies such as antinuclear and anti T cell membrane antibodies. Therefore the result of the assay does not always indicate the presence of the ATL virus antibodies. For example, when the serum of a systemic lupus erythematodes patient is employed as a specimen, said specimen, which is inherently negative to ATL virus antibodies, would sometimes show a positive result. The positive result might be thought to be caused by a reaction between antibodies accompanying the systemic lupus erythematodes and a non-specific component in the ATL associated antigen.

In order to overcome the abovementioned problem, Japanese Patent Application No. 144874/1983 has provided a process wherein an antigen independently prepared by treating an appropriate ATL virus negative cell strain obtained, e.g., by treating a cell strain derived from an acute lymphoblastic leukemia patient is employed in assaying and the result thus obtained is used as a comparison in the judgement to prevent misassaying caused by non-specific antibodies. However, the foregoing invention is yet open to question. That is, it can not ensure that the non-specific antibodies detected by the ATL associated antigen and by the antigen derived from the ATL virus negative cell strain are immunologically identical. Rather, it must be thought that the two antibodies are different from each other. Accordingly, the presence or absence of the latter does not always reflect the presence or absence of the former and the judgement of the presence of the ATL virus antibodies according to the above-mentioned invention is ambiguous.

As described above, the process for assaying ATL virus antibodies disclosed by Japanese Patent Application No. 144874/1983 is useful in practically judging the presence of said antibodies, but it is yet open to question. Under these circumstances we attempted to discover a process for exactly assaying ATL virus antibodies. As a result of our studies, we have found that the foregoing object can be achieved by independently preparing a comparative specimen by adding an ATL virus antigen to the test specimen and subtracting the result obtained by using the control specimen from that obtained by using the test specimen, thus leading to the completion of the present invention.

Accordingly, it is an object of the present invention to provide a reagent by which ATL-virus antibodies in a specimen can be exactly assayed in the prevention and treatment of adult T cell leukemia. In order to achieve the above object, the present invention discloses a process for assaying ATL virus antibodies, which is characterized in that a specimen prepared by adding an ATL virus antigen to the test specimen is employed as a comparative specimen and a reagent therefor.

Now the present invention will be described in detail.

The ATL associated antigen relating to the present invention is the so-called adult T cell leukemia associated antigen. More particularly, it occurs in the form of antigen proteins or C-type viral particles in ATL associated antigen producing cells. It specifically reacts with ATL virus antibodies, if present. The ATL virus associated antigen may be prepared by treating an antigen producing cell strain such as MT-2 cells with a surfactant. MT-2 cells are well known in the art. They originate from human funic leukocytes. They are established by a mixed culture with leukemia cells collected from the peripheral blood of an adult T cell leukemia patient. Further description of the ATL associated antigen and the process for treating the MT-2 with a surfactant are found in the following literature references.

(7) Yoshida, M., et al., Proc. Nat. Acad. Sci., 79, 2031 (1982).
(8) Miyoshi, I., et al., Gann, 72, 978 (1981).
(9) Miyoshi, I., et al., Nature, 294, 770 (1981).
(10) Japanese Patent Application No. 169670/1982.

The ATL virus antigen relating to the present invention is an antigen peculiar to said virus and originates from pathogenic viral particles of adult T-cell leukemia.

It specifically reacts with ATL virus antibodies, if present. The ATL virus antigen may be prepared by treating ATL virus, which is prepared by concentrating the supernatant of a medium wherein ATL antigen producing cells are cultured followed by purification, with a surfactant. For example, the supernatant of a medium wherein MT-2 cells are cultured is concentrated and ultracentrifuged to separate ATL virus, the ATL virus thus collected is further subjected to sucrose concentration gradient ultracentrifugation to fractionate and antigen positive fractions among them are dialyzed to thereby give purified ATL virus. The purified ATL virus thus obtained is treated by adding sodium deoxycholate thereto and dialyzed to give the ATL virus antigen.

The producing cells for preparing the ATL associated antigen and those for preparing the ATL virus and the ATL virus antigen are not necessarily identical. However it is desirable that the two antigens, as described above, are prepared from the same producing cells in the present invention since the ATL virus antigen according to the present invention is employed to prepare a comparative specimen in the assay with the use of the ATL associated antigen.

The treatment of the ATL antigen producing cells or the ATL virus to give the ATL associated antigen or the ATL virus antigen respectively may be carried out in any way. For example, a treatment with a surfactant such as sodium deoxycholate, octylphenoxypolyethoxyethanol and polyoxyethylene (10) octylphenyl ether may be performed. The treatment with a surfactant is described in detail in Japanese Patent Laid-Open No. 62527/1984.

Now the assay process of the present invention will be described in detail.

The process of the present invention is carried out by a method selected from among enzyme immunoassay, radioimmunoassay and passive hemagglutination. The general procedures in these methods are well known per se. For Example, the process of the present invention by enzyme immunoassay may be carried out as follows.

The whole assay system comprises a solid phase, an ATL associated antigen, an ATL virus antigen, a specimen, an antihuman IgG antibody to be labelled, an enzyme and a substrate. Examples of the solid phase are a cup of a microtiter plate for enzyme immunoassay or a glass bead. Prior to the assay, the ATL associated antigen is dissolved in a 0.15M phosphate buffer physiological saline solution, introduced into, e.g., a polystyrene cup for enzyme immunoassay and allowed to stand overnight at 4° C. to thereby coat the surface of the solid phase with the ATL associated antigen.

Examples of the antihuman IgG antibody to be labelled are goat antihuman IgG and mouse antihuman Fc monoclonal antibodies. Examples of the enzyme are alkali phosphatase, glucose oxidase, peroxidase and $\beta$-galactosidase. Prior to the assay, the antibody to be labelled may be combined with the enzyme with the use of a binder such as glutaraldehyde to form a conjugate, thus providing one of the reagents for the assay process of the present invention.

The substrate may be optionally selected depending on the enzyme to be used. For example, when alkali phosphatase is selected as the enzyme, p-nitrophenyl phosphate or similar substrates may be employed.

The elements of the whole assay system other than the specimen and the ATL virus antigen as cited above are shown to illustrate preferred embodiments of the present invention and not by way of limitation.

The specimen is most frequently available as a serum specimen obtained, e.g., from transfusion blood. However the present invention is not limited thereby and any specimen is usable regardless of the form or origin thereof. The specimen may be added to the assay system as such. Alternately it may be diluted with, e.g., normal rabbit serum (NRS) to an appropriate concentration prior to the assay.

The ATL virus antigen may be added to the assay system as such, although it is desirable to dilute it to an appropriate concentration with NRS. However dilution should be avoided since it might give inconsistent results. Accordingly, it is necessary to determine the optimum dilution ratio with the use of ATL virus antibody positive serum. For example, the protein concentration of the ATL virus antigen prepared in Experimental Example 1 as will be shown below was 1.23 at $OD_{280}$ nm. In this case, it is best to dilute it 16-fold with NRS. Two specimens, i.e., the test and control specimens are assayed. The latter is prepared by adding an ATL virus antigen to the former. However, it is generally required to dilute each specimen to an appropriate concentration with, e.g., NRS in order to facilitate the assay and to minimize errors. In this case, not only the test and control specimens, but also a control specimen comprising only the solvent, should be prepared and assayed.

The assay may be carried out according to the usual procedures of enzyme immunoassay. Thus, each of the test, comparative and control specimens is introduced into a cup coated with an ATL associated antigen and incubated therein. An antibody labelled with an enzyme, e.g., goat antihuman IgG/alkali phosphatase conjugate is added thereto and incubated therein. A substrate, e.g., p-nitrophenyl phosphate is added thereto and incubated therein and the amount of the decomposed substrate is determined with a spectrophotometer.

Finally the repression ratio (%) is calculated with the use of the data A, B and C obtained from the test, comparative and control specimens, respectively:

*Repression ratio* $(\%) = (A-B)/(A-C) \times 100$.

It is possible to assay ATL virus antibodies in a test specimen by determining the repression ratio (%) with the use of a specimen containing a known amount of ATL virus antibodies and drawing a calibration curve of the repression ratio (%).

It is further possible to exactly and unambiguously determine the presence of ATL virus antibodies in a specimen (test serum) based on a criterion that the specimen is positive with respect to the ATL virus antibody when the repression ratio is 50% or above, while it is negative when the ratio is less than 50%.

According to the process of the present invention, it is possible to distinguish between ATL virus antibody positive and negative serums.

The present invention further provides a reagent which essentially comprises an ATL associated antigen and ATL virus antigen.

The reagent of the present invention is directly available in the process of the present invention as described above to thereby achieve the same object as that of the foregoing process.

The reagent of the present invention may be used in any of enzyme immunoassay, radioimmunoassay and passive hemagglutination. For example, the reagent of the present invention may be practically used in enzyme immunoassay in the following manner. The reagent of the present invention is in the form of a combination of an ATL associated antigen and an ATL virus antigen as such or a set comprising one to four elements arbitarily selected from among an ATL associated antigen and an ATL virus antigen, a solid phase, an antibody to be labelled, an enzyme and a substrate. When the set comprises a solid phase, the solid phase may be coated with the ATL associated antigen. When the set comprises an antibody to be labelled and an enzyme, these two materials may be in the form of a conjugate, i.e., a labelled antibody. It should be noted that these cases are also in the scope of the present invention. It should be also noted that the set may further comprise an appropriate buffer or NRS in order to facilitate the assay without departing from the scope of the present invention.

To further illustrate the present invention, the following examples will be given.

EXAMPLE 1

A 0.15M phosphate buffer physiologically saline solution (pH 7.2) was added to $2.4 \times 10^7$ MT-2 cells and the mixture was centrifuged to separate the cells which were then packed. 5 ml of a veronal buffer solution (pH 7.5, $\mu=0.145$) containing 0.2% of sodium deoxycholate was added thereto and the obtained mixture was stirred with a stirrer at 4° C. for four hours and subsequently centrifuged at 10,000 rpm for 30 min. The supernatant was poured in a dialysis tube, dialyzed against a 0.15M phosphate buffer physiololigal saline solution at 4° C. for two days and subsequently centrifuged at 10,000 rpm for 30 min. The supernatant thus obtained was referred to as a supernatant containing an ATL associated antigen. The $OD_{280}$ value of the above supernatant was 15/ml.

The obtained serum containing the ATL associated antigen was diluted with a 0.15M phosphate buffer physiological saline solution to give an $OD_{280}$ value of 0.4. 150 μl portions of the solution were introduced into polystyrene enzyme immunoassay cups.

Each cup was allowed to stand overnight at 4° C., then drained and washed with deionized water. The cup thus prepared was combined with a goat antihuman IgG antibody/alkali phosphatase conjugate, p-nitrophenyl phosphate and an ATL virus antigen to give a set. This set was a reagent for enzyme immunoassay. In order to facilitate the assay, the set further comprised NRS, a 0.9% sodium chloride solution and 1N—NaOH.

The ATL virus antigen was prepared as follows. 3 l of the supernatant of a medium wherein MT-2 cells were cultured was centrifuged at 10,000 rpm for 30 min to collect the supernatant which was subsequently concentrated and centrifuged under 10,000 G for two hours. ATL virus was collected as a precipitate. The precipitate was then thoroughly suspended in 4 ml of a 0.01M tris-hydrochloride buffer solution (pH 7.5) containing 0.15M of NaCl, 0.002 M of EDTA and 0.1% of $NaN_3$ and the obtained suspension was centrifuged at 10,000 rpm for 30 min to collect the supernatant as a crude viral concentrate. 45 ml of a sucrose concentration gradient solution (15 to 60% by weight) was prepared in a nitrocellulose tube and 2 ml of the above crude viral concentrate was laminated thereon and ultracentrifuged at 22,000 rpm for 15 hours with an RPS-25-2 rotor (Hitachi). Then, 50 drop (ca. 2 ml) portions of the eluent were collected from the bottom of the tube. The ATL virus in each fraction was assayed by enzyme immunoassay wherein human ATLA antibodies were used as inhibition antibodies. ATL virus positive fractions were combined and dialyzed against a 0.01 M tris-hydrochloride buffer solution (pH 7.5) containing 0.15M of NaCl, 0.002M of EDTA and 0.1% of $NaN_3$ to give 1.15 g/ml of an ATL virus solution. After completing the dialysis, sodium deoxycholate was added thereto to give a concentration of 0.2% and the obtained mixture was stirred at 4° C. for 30 min. Then it was dialyzed against a 0.01M trishydrochloride buffer solution (pH 7.5) containing 0.15M of NaCl, 0.002M of EDTA and 0.1% of $NaN_3$ to remove sodium deoxycholate, thus giving an ATL virus antigen. Thus, 35 ml of the ATL virus antigen containing 1.23 of protein at $OD_{280\ nm}$ was collected.

EXAMPLE 2

Goat antihuman IgG antibody or mouse antihuman IgG (Fc) antibody was dissolved in a 0.05M phosphate buffer solution (pH 7.5) to give a protein concentration of 1 mg/ml. To 10 μl of the solution thus obtained were successively added an effective amount of $125_{I-Na}$ of 1 mCi and 10 μl of a solution prepared by adding 1.5 mg/ml of chloramine T to the foregoing phosphate buffer solution, and the obtained mixture was stirred for 30 sec. Subsequently 100 μl of a solution prepared by dissolving 2 mg/ml of sodium hydrogen metasulfate in the foregoing phosphate buffer solution was added thereto to thereby stop the reaction. 100 μl of a solution prepared by dissolving 10 mg/ml of potassium iodide in the foregoing buffer solution was added to the reaction liquor and the mixture was immediately subjected to gel filtration with Sephadex G-50 to separate the $^{125}$I-labelled substance from the $^{125}$I. The $^{125}$I-labelled substance exhibited a specific radioactivity of approximately 5 to 20 μCi/μg.

This $^{125}$I-labelled substance was combined with a cup and an ATL virus antigen both prepared in the same manner as described in Example 1 to give a set which was available in radio immunoassay.

EXAMPLE 3

Sheep blood was centrifuged at 2,000 rpm for 10 min five times in a tube with the use of a physiological saline solution to wash erythrocytes therein. To the erythrocytes was added a 0.15M phosphate buffer physiological saline solution (pH 7.5) to give a concentration of 5%. A glutaraldehyde solution adjusted to a concentration of 2.5% with the foregoing phosphate buffer physiological saline solution was added to the above erythrocyte suspension in an amount of one-fifth by volume. The obtained mixture was allowed to react at room temperature under stirring for approximately five hours to thereby fix the erythrocytes. Then the solution was centrifuged to give fixed erythrocytes, which were then washed with a physiological saline solution several times with the use of a centrifuge. The fixed erythrocytes were subsequently adjusted to a 5% suspension with the foregoing phosphate buffer solution and the same amount of a tannic acid solution adjusted to a concentration of 5 mg/dl with the foregoing phosphate buffer physiological saline solution were added thereto followed by stirring for 30 min. The solution thus obtained was centrifuged to give fixed erythrocytes treated with tannic acid, which were then further centrifuged several times with the use of a physiological saline solution. The foregoing phosphate buffer solution was added to the obtained fixed erythrocytes treated with tannic acid to give a 5% erythrocyte suspension.

The erythrocyte suspension thus obtained was mixed with the same amount of a solution prepared by diluting the supernatant containing an ATL associated antigen as prepared in Example 1 with the foregoing phosphate buffer physiological saline solution to give a protein concentration of approximately 5 mg/ml and the mixture was sensitized by stirring at room temperature for 60 min. The obtained solution was centrifuged to give sensitized erythrocytes, which were then washed with a physiological saline solution by centrifuging several times. To the sensitized erythrocytes thus obtained was added a phosphate buffer physiological saline solution containing 2% of NRS to give a 7% suspension. The sensitized erythrocytes were combined with the ATL virus antigen as prepared in Example 1 to give a reagent for passive hemagglutination.

EXAMPLE 4

A serum specimen was judged as ATL virus antibody positive or negative with the use of the reagent set as prepared in Example 1.

100 µl portions of NRS and an ATL virus antigen solution which was prepared by diluting 16-fold the ATL virus antigen as shown in Example 1 with NRS were independently introduced into test tubes. 20 µl of the serum specimen was introduced into each tube. The former was referred to as the test specimen while the latter as a comparative specimen. Separately NRS was prepared as such to give a control specimen.

Each specimen was thoroughly stirred and allowed to stand at 37° C. for one hour or at 4° C. overnight. Then 100 µl of each specimen was introduced into a coated cup as shown in Example 1 and incubated at 37° C. for 60 min. After the completion of the incubation, a 0.9% sodium chloride solution was added thereto to wash out unreacted matters and 100 µl of a goat antihuman IgG/alkali phosphatase conjugate solution was added to the reaction mixture. After reincubating at 37° C. for 60 min, a 0.9% sodium chloride solution was added thereto to wash out unreacted matters and 100 µl of p-nitrophenyl phosphate solution was added to the reaction mixture. The mixture was reacted at 37° C. for 30 min and subsequently 100 µl of 1N NaOH was added thereto to stop the reaction. Finally the optical density of each sample was determined at 405 nm. The optical density of the test specimen was referred to as A, that of the comparative specimen as B, while that of the control specimen as C. The repression ratio (%) was calculated from A, B and C according to the following equation:

*Repression ratio* $(\%) = (A-B)/(A-C) \times 100$.

When the repression ratio is 50% or above, the serum specimen is positive with respect to ATL virus antibodies, while when it is lower than 50%, the specimen serum is negative.

To furthermore illustrate the effect of the present invention, the following Experimental Examples will be given.

EXPERIMENTAL EXAMPLE 1

As shown in Table 1, serum specimens Nos. 1 to 11 were prepared. It had been confirmed that Nos. 1 to 5 and Nos. 6 to 11 were, respectively, positive and negative with respect to ATL virus antibodies by immunofluorescent antibody assay. Among these negative serums, Nos. 6 to 8 were normal human serums (NHS) while Nos. 9 to 11 were derived from systemic lupus erythematodes patients.

Each serum specimen was assayed in the same manner as described in Example 4 and the repression ratio (%) thereof was calculated from A, B and C to thereby judge the specimen whether it is positive or negative with respective to ATL virus antibodies according to the manner as described in Example 4. Table 1 shows the result. Table 1 suggests that the assay method of the present invention can give an unambiguous and exact judgement on ATL virus antibodies. It is particularly remarkable that serum specimens Nos. 9 to 11, which are inherently negative with respect to ATL virus antibodies, are misunderstood to be positive in a conventional manner wherein the judgement is based on only A while the process of the present invention based on the repression ratio gives correct judgement and clearly distinguishes them from true positive as shown in Table 1. It is a characteristic advantage of the present invention.

TABLE 1

| Serum Specimen No. | IF Judgement* | Data A | B | C | Repression Ratio (%) | Judgement by the Process of the Invention |
|---|---|---|---|---|---|---|
| 1 | + | 1.291 | 0.295 | 0.019 | 78.3 | Positive |
| 2 | + | 0.296 | 0.022 | 0.019 | 98.9 | " |
| 3 | + | 0.142 | 0.046 | 0.019 | 78.0 | " |
| 4 | + | 1.649 | 0.124 | 0.021 | 93.7 | " |
| 5 | + | 0.612 | 0.043 | 0.021 | 96.3 | " |
| 6 | − | 0.031 | 0.031 | 0.021 | 0 | Negative |
| 7 | − | 0.033 | 0.031 | 0.021 | 16.7 | " |
| 8 | − | 0.032 | 0.036 | 0.021 | 0 | " |
| 9 | − | 0.132 | 0.166 | 0.019 | 0 | Positive |
| 10 | − | 0.115 | 0.113 | 0.019 | 2.1 | " |
| 11 | − | 0.142 | 0.136 | 0.019 | 4.9 | " |

*If judgement refers to a judgement by immunofluorescent antibody assay and + and −, respectively, represent positive and negative with respect to ATL virus antibodies in the above judgement.

EXPERIMENTAL EXAMPLE 2

To illustrate the method for determining the optimum dilution ratio of an ATL virus antigen, the present example will be given.

The ATL Virus antigen as obtained in Experimental Example 1 was diluted $2^n$-fold (i.e. 2 to 128-fold) with 100 µl of NRS. Separately NRS as such was prepared. To each specimen was added 20 µl of human ATL virus antibodies positive serum, and the mixture was incubted at 37° C. for one hour or at 4° C. overnight. Then 100 µl of the reaction mixture was introduced into a coat cup of the reagent set as shown in Example 1 and the OD value of the comparative specimen, i.e. B, was determined according to the procedures as described in Example 4. The C of each NRS used in diluting was determined according to the procedures as shown in Example 4.

Table 2 shows the result. NRS in the dilution ratio column of Table 2 refers to normal rabbit serum used as the control which is negative to with respect ATL virus antibodies. Table 2 indicates that the repression due to the ATL virus antigen attains equilibrium and affords a consistent data when diluted 16-fold.

TABLE 2

| Dilution ratio | Data B | Data C |
|---|---|---|
| NRS | 0.437 | 0.019 |
| 1:128 | 0.075 | 0.018 |

TABLE 2-continued

| Dilution ratio | Data B | Data C |
| --- | --- | --- |
| 1:64 | 0.054 | 0.019 |
| 1:32 | 0.042 | 0.019 |
| 1:16 | 0.035 | 0.018 |
| 1:8 | 0.038 | 0.020 |
| 1:4 | 0.035 | 0.019 |
| 1:2 | 0.035 | 0.018 |

The embodiments of the invention in which an exclusive property or privilege is claimed are defined as follows:

1. In a process for assaying an ATL virus antibody in a test specimen by a method selected from the group consisting of the enzyme linked immunosorbent assay, the radioimmunoassay and the passive hemagglutination assay, in which the test specimen and a control specimen are separately subjected to an antibody-antigen reaction using an immobilized ATL associated antigen and the extent of said reaction is determined, wherein the improvement comprises: preparing a comparative specimen by adding an ATL virus antigen to a second test specimen to bind any ATL antibodies present in said second test specimen, separately subjecting said comparative specimen to said antibody-antigen reaction using said ATL associated antigen and determining the extent of said reaction and comparing the extent of reaction of said test, control and comparative specimens as a measure of ATL virus in the test specimen.

2. A process as claimed in claim 1, in which the ATL associated antigen originates from MT-2 cells.

3. A process as claimed in claim 1, in which the ATL virus antigen originates from MT-2 cells.

4. A process as claimed in claim 1, in which the enzyme linked immunosorbent assay is used and the optical densities of the reaction products of said antibody-antigen reaction are measured to give the value A for the test specimen, the value B for the comparative specimen and the value C for the control specimen and then calculating $$\text{repression ratio (\%)} = \frac{(A - B)}{(A - C)} \times 100,$$

wherein the test specimen is positive with respect to ATL virus antibodies when the repression ratio is 50% or higher and is negative when the repression ratio is less than 50%.

* * * * *